United States Patent [19]

Marchi et al.

[11] 4,200,574

[45] Apr. 29, 1980

[54] RIFAMYCIN DERIVATIVES AND PROCESS FOR THEIR PREPARATION

[75] Inventors: Egidio Marchi; Lauretta Montecchi, both of Casalecchio Di Reno, Italy

[73] Assignee: Alfa Farmaceutici, S.p.A., Bologna, Italy

[21] Appl. No.: 968,410

[22] Filed: Dec. 11, 1978

[30] Foreign Application Priority Data

Dec. 20, 1977 [IT] Italy .................................. 3654 A/77

[51] Int. Cl.$^2$ ..................... C07D 491/08; A61K 31/33
[52] U.S. Cl. .............................. 260/239.3 P; 424/244
[58] Field of Search ................................. 260/239.3 P

[56] References Cited

U.S. PATENT DOCUMENTS

| | | | |
|---|---|---|---|
| 3,342,810 | 9/1967 | Maggi et al. | 260/239.3 P |
| 3,349,082 | 10/1967 | Maggi et al. | 260/239.3 P |

Primary Examiner—John D. Randolph
Assistant Examiner—Robert T. Bond
Attorney, Agent, or Firm—Stevens, Davis, Miller & Mosher

[57] ABSTRACT

8-amino and 8-iminorifamycins S and SV are prepared by reacting 8-methoxyrifamycin S with ammonia in an inert polar and hydrophillic solvent, converting the 8-iminorifamycin S into 8 aminorifamycin S by reaction with ammonium hydroxide in a mixture of chloroform and methanol and, if so desired, reducing the S forms to SV forms by reduction.

7 Claims, No Drawings

RIFAMYCIN DERIVATIVES AND PROCESS FOR THEIR PREPARATION

DETAILED DESCRIPTION OF INVENTION

The present invention refers to 8-amino and 8-iminorifamycin S and SV and to the process for their preparation.

The structure of rifamycin S and SV is widely known and therefore in the description of the present invention will be used structural formulae which represent only the aromatic part of their molecule. Both rifamycin S and SV have in the position 8 an hydroxy group.

Subject of the present invention are derivatives of rifamycin S and SV which present in the 8 position, in the place of the hydroxy group, an amino or an imino group.

To 8-aminorifamycins SV and S it is possible to ascribe the following structural formulae:

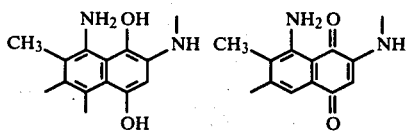

8-aminorifamycin SV    8-aminorifamycin S

For the 8-iminorifamycin S it is possible, on the basis of the chemical behaviour, of the spectra, of the physicochemical characteristics to hypothesize the following structural formulae:

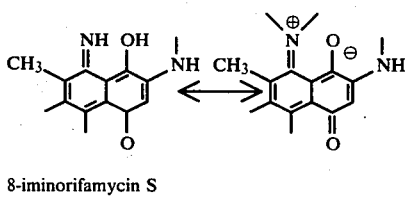

8-iminorifamycin S

It is much more difficult to express an hypothesis about the structure of the reduced form of the 8-iminorifamycin S which, for simplicity's sake, we have indicated as 8-iminorifamycin SV.

In fact, by reduction of 8-iminorifamycin S under identical conditions to those usually adopted for converting the rifamycins S to rifamycins SV (for instance, reduction with ascorbic acid) a well defined product is obtained which is not any longer the 8-iminorifamycin S, which is different from 8-aminorifamycin and which by oxidation under conditions identical to those usually adopted for converting the forms SV to forms S (for instance oxidation with manganese dioxide) give again the 8-iminorifamycin S.

The 8-amino and the 8-iminorifamycins S and SV show an antibacterial activity comparble to that of the rifamycins S and SV. Furthermore they are useful intermediate for the preparation of derivatives having in the 8 position other substituents and possessing antibacterial and antiviral activity.

Subject of the present invention is also the process for the preparation of 8-amino and 8-iminorifamycins S and SV which consists in reacting the 8-methoxyrifamycin S with an excess of ammonia in the presence of at least one inert, hydrophillic and polar solvent, or a mixture of said solvent with water at a temperature comprised between the room temperature and 60° C., in recovering separately from the reaction mixture the 8-iminorifamycin S and the 8-aminorifamycin S occasionally formed and, if so desired, in converting said 8-iminorifamycin S in 8-aminorifamycin S by reaction with an excess if aqueous ammonium hydroxide in the presence of a mixture of methanol and chloroform, at a temperature comprised between the room temperature and 60° C. and, if so desired, in reducing said 8-iminorifamycin S and said 8-aminorifamycin S respectively to 8-iminorifamycin SV and 8-aminorifamycin SV by treatment with mold reducing agents according to known techniques.

In the reaction of 8-methoxyrifamycin S with ammonia as well as in the transformation of 8-iminorifamycin S to 8-aminorifamycin S, it is preferred to operate at temperature above the room temperature as under such conditions the reaction time is sensibly decreased.

Under such conditions, and particularly when are used temperatures near to the upper limit of the above indicated temperature range, it becomes necessary to carry out the reaction in a closed vessel.

The solvent used in the process according to the present invention are inert, polar, hydrophillic solvents. Examples of such solvents are: methanol, ethanol, acetonitrile, dioxane, dimethylsulfoxide, tetrahydrofuran.

It has been observed that under same reaction conditions, the nature of the solvent has a certain influence on the ratio between the obtained 8-imino and the 8-aminorifamycin S. In fact, whereas in some solvents the formation of 8-iminorifamycin S is promoted, in other solvents, mixtures of 8-imino and 8-aminorifamycin S containing sensible amounts of the last are formed.

In the conversion reaction of the 8-iminorifamycin S in 8-aminorifamycin S one works in the presence of a mixture of methanol and chloroform. Although it is possible to work with mixtures of rather wide composition, it is preferred to work with mixtures containing approximately 25% of chloroform.

It has been observed, in fact, that mixtures containing more chloroform give rise to a separation of the two solvents and therefore require a vigorous stirring and longer reaction times. On the other hand mixtures containing more methanol do not allow the complete solution of the starting 8-iminorifamycin S and require therefore greater volumes of solvent.

The conversion of the forms S into the forms SV is carried out according to known techniques in the field of rifamycins and their derivatives, by treatment, in the presence of suitable solvents, with mild reducing agents.

Examples of such reducing agents are ascorbic acid, sodium hydrosulfite, sodium thiosulfate etc.

The following examples are supplied with the purpose of illustrating the present invention.

The thin layer chromatographies (TLC) therein referred have been carried out on layer of silica gel 60 $F_{254}$ of a thickness 0,2 mm on aluminum plates (Merck).

The values of $Rf_R$ given for the products are referred to the Rf of rifamycin S.

The 8-methoxyrifamycin S used as starting product has been prepared according to Helv. Chimica Acta 56,7,2305 (1973) and purified in a column of silica gel 60, 70–230 mesh ASTM (Merck), using as solvent both for seeding and for eluting a mixture ethylether/methanol 24/1 (v/v).

EXAMPLE 1

Preparation of the 8-iminorifamycin S 4 ml of a solution saturated at 0° C. of ammonia in acetonitrile are added to 200 mg of 8-methoxyrifamycin S, dissolved in 6 ml of acetonitrile. After stirring at 40° C. for 8 hours a red violet product is obtained that on TLC (eluent ethylether/methanol: 24/1 v/v) shows a $Rf_F=0.48$. The reaction is stopped by bringing a dryness and the residue is crystallized from 3 ml of methanol. 145 mg of 8-iminorifamycin S are obtained (yield 72% of the theory).

UV Spectrum in methanol nm 215 (log $\epsilon$=4,46), 254 (4,33) shoulder, 308 (4,38), 340 (3,76) shoulder, 487 (3,61).

IR Spectrum in chloroform, peaks at: 3490 (strong), 3440 (medium), 3340 and 3320 (s), 2980–2820 (s), 1725 and 1705 (s), 1650 (s), 1620 (s), 1560 (s), 1490 (s), etc. (in $cm^{-1}$).

NMR Spectrum in $CDCl_3$: δ0,2 ppm (d), 0,6–1,2 (m), 1,5–2,3 (m), 1,75 (s), 2,08 (s), 2,22 (s), 3,0–4,1 (m), 3,13 (s), 3,50 (s), 4,8–5,3 (m), 6,1–6,5 (m), 7,95 (s), 9,02 (s).

Elemental analysis: C%=62,80, H%=6,51, N%=3,97 calculated for $C_{37}H_{46}N_2O_{11}$ C%=63,96, H%=6,67, N%=4,03.

Potentiometric titration: the product behaves as an acid therefore it is titurated in a mixture of acetonitrile/-pyridine 4/1, with tetra n-butylammonium hydroxide 0,1 N, titre of the final product 98,5%.

EXAMPLE 2

Preparation of 8-imino and 8-aminorifamycin S 5 ml of a saturated solution at 0° C. of ammonium in methanol are added to g 1,0 of 8-methoxyrifamycin S dissolved in 30 ml methanol. The mixture is heated in a closed vessel for 1 hour at 55° C. On TLC (chloroform-/methanol 24/1 v/v) two main spots can be observed: one at $Rf_R=0,63$ (corresponding to 8-imino) and another at $Rf_R=0,47$ brown, (corresponding to 8-amino). By cooling the reaction mixture g 0,466 of 8-aminorifamycin S crystallize out.

After filtration and bringing to dryness the filtrate, the residue is crystallized from methanol.

Further g 0,190 of 8-aminorifamycin S are obtained. The overall yield for this product is 66% of the theory.

The residue is purified in a column of silica gel 60, 70–230 mesh ASTM (Merck) of inner diameter 2,5 cm and 30 cm of height, using as eluent a mixture of chloroform/methanol=24/1 (v/v).

The fractions presenting $Rf_R=0,63$ are collected and evaporated to dryness. g 0,130 of 8-iminorifamycin S (yield 13,2% of the theory) are obtained.

The 8-aminorifamycin S shows the following characteristics:

UV Spectrum in methanol: 207 nm (log δ=4,47), 262 (4,36), 308 (4,46), 470 (3,63).

IR Spectrum in chloroform: peaks at 3490 (s), 3450 (m), 3350 and 3300 (m), 3200 (weak), 2980–2820 (m-s), 1720 (w), 1695 (s), 1640 (m), 1610 (s), 1570 and 1560 (m), etc. (in $cm^{-1}$).

NMR Spectrum in $CDCl_3$: δ0.15 ppm (d), 0,7–1,2 (m), 1,6–2,5 (m), 1,7 (s), 2,1 (s), 2,2 (s), 3–3,6 (m), 3,12 (s), 3,52 (s), 3,6–4,2 (m), 4,7–5,2 (m), 6,0–6,4 (m), 8,92 (s), 9,02 (s).

Elemental analysis: C%=60,97, H%=6.47, N%=3,95 calculated for $C_{37}H_{46}N_2O_{11}$ C% 63,96, H%=6,67, N%=4,03.

Potentiometric tritration: the compound behaves as a weak base and is therefore titrated in acetic acid with perchloric acid O,IN; titre 99%.

EXAMPLE 3

100 ml of ammonium hydroxide 32% are added to 10 g of 8-methoxyrifamycin S dissolved in 200 ml dimethylsulfoxide. After stirring at room temperature for 90 minutes and after having vented off the ammonia under vacuum, 300 ml water are added and the mixture is extracted with chloro form. The organic phase is dried and brought to dryness. The residue is crystallized from methanol g 7,95 of 8-iminorifamycin (yield 81% of theory) are obtained.

The crystallization methanol contains still some product which can be recovered by purification by chromatography in a column of silica gel.

The reaction has been repeated by heating for 30 minutes the reaction mixture up to 65° C. in a closed vessel, obtaining the same yield.

EXAMPLE 4

Preparation of 8-aminorifamycin S 7 ml methanol and subsequently 2,3 ml of ammonium hydroxide at 32% are added to 1,4 g of 8-iminorifamycin S dissolved in 3 ml chloroform.

The mass is kept at 60° C. in a closed vessel for 40 minutes. The ammonia is vented off under vacuum and concentrating, in the same time, the solution to one third of the original volume.

50 ml chloroform are added and the organic solution is washed with water, dried and brought to dryness.

The residue is crystallized from ethanol and g 1,280 of 8-aminorifamycin S (yield 92% of theory) are obtained.

EXAMPLE 5

Preparation of 8-aminorifamycin SV g 0,6 of ascorbic acid in aqueous solution are added under stirring to g 1 of 8-aminorifamycin S dissolved in ethylacetate. After 15 minutes the phases are separated and the organic layer is washed repeatedly with water, dried, and brought to dryness.

g 1 of 8-aminorifamycin SV is obtained. The compound can be titrated as a base like the 8-aminorifamycin S.

EXAMPLE 6

Preparation of 8-iminorifamycin SV

Starting from g 1 of 8-iminorifamycin S is ethylacetate and working as in Example 5 g 1 of 8-iminorifamycin SV is obtained.

UV Spectrum in methanol: peaks at 218 nm (log $\epsilon$=4,51), 308 (4,37), 430 (3,90), 458 (3,91).

IR Spectrum in $CHCl_3$: peaks at 2490 $cm^{-1}$ (s), 3430 (s), 3390 (w), 3318 (s), 2980-2820 (m-s), 1710 (s), 1660 (shoulder), 1645 (w), 1585 (s), etc.

NMR Spectrum in $CD_3OD$=signals at δ=−0,22 (d) p.p.m., +0,72 (d), 0.94 (d), 1,04 (d), 1,5–2,5 (broad), 1,74 (s), 2,1 (singlet containing 3 methyls), 3,08 (s), 3,0–3,6 (multiplet), 3,8–4,2 (m), 4,8–5,3 (m), 6,2–6.9 (m).

EXAMPLE 7

Preparation of 8-aminorifamycin S by oxidation of the form SV

An excess of manganese dioxide (prepared according to Rosenkranz) is added to 8-aminorifamycin SV dissolved in ethylacetate.

After stirring for 15 minutes, filtration of the dioxide and washing with water, the organic layer is dried and brought to dryness.

The residue is crystallized from ethanol obtaining the 8-aminorifamycin S.

EXAMPLE 8

Preparation of 8-iminorifamycin S by oxidation of the form SV

The 8-iminorifamycin S is obtained starting from 8-iminorifamycin SV and working as described in Example 7. The product is crystallized from methanol.

We claim:
1. 8-iminorifamycin S.
2. 8-aminorifamycin S.
3. 8-iminorifamycin SV.
4. 8-aminorifamycin SV.
5. Process for the preparation of 8-amino and 8-iminorifamycin S and SV consisting in reacting 8-methoxyrifamycin S with an excess of ammonia in the presence of at least one inert, polar and hydrophillic solvent or of a mixture of said solvent with water at a temperature comprised between the room temperature and 60° C., in recovering separately from the reaction mixture the 8-iminorifamycin S and the 8-aminorifamycin S occasionally formed and, if so desired, in transforming said 8-iminorifamycin S in 8-aminorifamycin S by reaction with an excess of ammonia in the presence of a mixture of methanol and chloroform, at a temperature comprised between the room temperature and 60° C. and, if so desired, in reducing said 8-iminorifamycin S and said 8-aminorifamycin S respectively to 8-iminorifamycin SV and 8-aminorifamycin SV by treatment with mild reducing agents, according to known techniques.

6. Process according to claim 5 wherein said inert, polar and hydrophillic solvent is selected from the group comprising: methanol, ethanol, acetonitrile, dioxane, dimethysulfoxide and tetrahydrofuran.

7. Process according to claim 5, wherein the transformation of said 8-iminorifamycin S to said 8-aminorifamycin S is carried out in the presence of a mixture of methanol and chloroform containing about 25% of chloroform.

* * * * *

UNITED STATES PATENT AND TRADEMARK OFFICE
CERTIFICATE OF CORRECTION

PATENT NO. : 4,200,574

DATED : April 29, 1980

INVENTOR(S) : MARCHI et al

It is certified that error appears in the above-identified patent and that said Letters Patent are hereby corrected as shown below:

In column 1, the second formula lacks a double bond; the correct formula is:

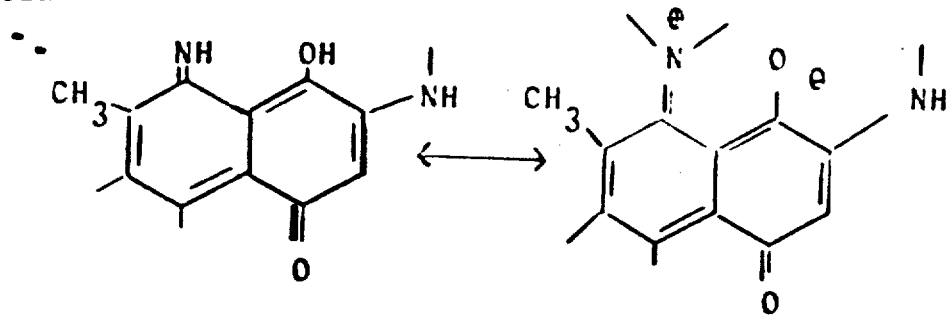

Column 3, line 9, delete "$Rf_F$" and insert --$Rf_R$--.

Signed and Sealed this

Sixteenth Day of December 1980

[SEAL]

Attest:

SIDNEY A. DIAMOND

Attesting Officer

Commissioner of Patents and Trademarks